(12) United States Patent
Pelerin

(10) Patent No.: US 6,494,717 B1
(45) Date of Patent: Dec. 17, 2002

(54) CALCIFIED TISSUE FACING PREPARATION CONTAINING AN ANTIMICROBIAL AGENT

(75) Inventor: Joseph J. Pelerin, Clarkston, MI (US)

(73) Assignee: Advantage Dental Products, Inc., Lake Orion, MI (US)

( * ) Notice: Subject to any disclaimer, the term of this patent is extended or adjusted under 35 U.S.C. 154(b) by 0 days.

(21) Appl. No.: 09/806,041

(22) PCT Filed: Sep. 23, 1999

(86) PCT No.: PCT/US99/21265

§ 371 (c)(1),
(2), (4) Date: Mar. 26, 2001

(87) PCT Pub. No.: WO00/16712

PCT Pub. Date: Mar. 30, 2000

Related U.S. Application Data

(60) Provisional application No. 60/101,655, filed on Sep. 24, 1998.

(51) Int. Cl.⁷ .............................. A61K 6/08; C09K 3/00; A61C 5/00; C08L 1/26; B24D 11/00
(52) U.S. Cl. ................... 433/217.1; 424/49; 424/54; 424/401; 106/35; 433/217.2; 523/116
(58) Field of Search .......................... 424/49–58, 401; 106/35; 433/217.1; 523/116

(56) References Cited

U.S. PATENT DOCUMENTS

| | | | | |
|---|---|---|---|---|
| 3,925,543 A | * | 12/1975 | Donohue | |
| 3,934,002 A | * | 1/1976 | Haefele | |
| 4,883,534 A | * | 11/1989 | Sandham et al. | |
| 5,068,107 A | * | 11/1991 | Hollibush et al. | |
| 5,133,957 A | * | 7/1992 | Suh et al. | |
| 5,178,870 A | * | 1/1993 | Schaeken | |
| 5,180,577 A | * | 1/1993 | Polefka et al. | |
| 5,213,615 A | * | 5/1993 | Michl | |
| 5,270,351 A | * | 12/1993 | Bowen | |
| 5,304,369 A | * | 4/1994 | Rheinberger et al. | |
| 5,330,746 A | * | 7/1994 | Friedman | |
| 5,340,581 A | * | 8/1994 | Tseng et al. | |
| 5,393,516 A | * | 2/1995 | Rheinberger et al. | |
| 5,401,783 A | * | 3/1995 | Bowen | |
| 5,575,652 A | * | 11/1996 | Gaffar et al. | |
| 5,622,552 A | * | 4/1997 | Arnold | |
| 5,708,052 A | * | 1/1998 | Fischer et al. | |
| 5,738,113 A | * | 4/1998 | Connelly | |
| 5,851,551 A | * | 12/1998 | Tseng et al. | |
| 5,866,630 A | * | 2/1999 | Mitra et al. | |
| 5,876,208 A | * | 3/1999 | Mitra et al. | |
| 5,888,491 A | * | 3/1999 | Mitra et al. | |
| 5,945,087 A | * | 8/1999 | Nelson et al. | |
| 6,093,084 A | * | 7/2000 | Jeffries et al. | |
| 6,136,885 A | * | 10/2000 | Rusin et al. | |
| 6,312,668 B2 | * | 11/2001 | Mitra et al. | |
| 6,326,417 B1 | * | 12/2001 | Jia | |

FOREIGN PATENT DOCUMENTS

WO  89/10736  * 11/1989

* cited by examiner

*Primary Examiner*—Shep K. Rose
(74) *Attorney, Agent, or Firm*—Gifford, Krass, Groh, Sprinkle, Anderson & Citkowski, P.C.

(57) ABSTRACT

The present invention provides a calcified tissue facing preparation characterized by having a polymerizable resin, and an antimicrobial agent of formula (I) where $R_1$ is a hydrocarbon radical having between 1 and 16 carbon atoms, n is an integer between 1 and 8 inclusive and X is a halogen atom selected from fluorine, chlorine or bromine. It is appreciated that $R_1$ includes unsaturated hydrocarbon radicals, as well as heteroatom containing radicals. Preferably, the molecule of formula (I) is associated with an adduct species. A solvent and the complementary spectrum antimicrobial benzalkonium chloride are also optionally added. An antimicrobial oral rinse excluding the polymerizable resin contains at least 0.2% by weight of the antimicrobial agent.

27 Claims, No Drawings

CALCIFIED TISSUE FACING PREPARATION CONTAINING AN ANTIMICROBIAL AGENT

RELATED APPLICATIONS

This application claims priority of PCT/US99/21265 filed Sep. 23, 1999, which claims priority of U.S. Provisional Application No. 60/101,655 filed Sep. 24, 1998.

FIELD OF THE INVENTION

This invention relates to compositions for sealing calcified tissue substrates to inhibit infection and promote subsequent restorative material bonding; in particular, the invention is tailored to dentinal tubules, in order to prevent dentinal hypersensitivity and further to promote effective bonding of subsequent restorative dental materials such as amalgams, composites, resins and cementitious materials.

BACKGROUND OF THE INVENTION

Dental caries are a common disease of modern humankind. The treatment of dental caries involves the removal of the carious lesion by a number of means including mechanical drilling and light ablation. The ensuing removal of dentin brings the dental nerve endings contained within the pulp into proximity with the mouth. Filling the resulting cavity in order to isolate the nerve endings leaves the tooth susceptible to thermal hypersensitivity via thermal conduction through the filling as well as bacterial infection. Bacterial colonization of the filled cavity induces further caries formation and hypersensitivity.

Currently, polymeric resinous materials are widely used to fill cavities, as well as in cosmetic dentistry and corrective dental structures including brackets, braces, veneers, onlays, crowns, and the like. In adhering dental structures to tooth enamel, there are minor problems with thermal or bacterial hypersensitivity.

In contrast, when the dentin of a tooth is exposed as a result of cervical erosion or tooth decay, changes occur in the physical structure of the dentin. Whereas tooth enamel is a densified, nonporous substance, dentin is characterized by a porous structure containing thousands of dentinal tubules. The dentinal tubules extend outward from the tooth pulp and terminate at or before the tooth enamel. These tubules contain pressurized pulp fluid which seeps from the pulp when the ends of the tubules are exposed. Collagen fibers are also associated with the tubules.

Typically, neither cervical erosion nor drilling of dentin directly exposes the ends of the dental tubules. Cervical erosion surfaces are characterized by irregularities and hemispherical protrusions. The dentinal tubules are mostly filled with inorganic material although some maintain openings of various sizes. Drilling of dentin creates a debris field which is characterized by weakened and cracked dentin. Since the debris field is structurally unsound, adhering a restorative material thereto creates a weak filling.

The cleaning of dentin prior to bonding a material thereto is. thus highly advantageous. Typically, acid etching is used to decalcify the surface dentin and enlarge the openings of the tubules. Acid etching leaves behind the protruding collagen fibers that are associated with the dentinal tubes. These collagen fibers represent a substrate for bacterial colonization as well as a hydrophilic surface for the bonding of a polymeric resinous material. The acid etching solution is typically a 20–50% by weight solution of phosphoric acid, but also includes citric and nitric acids.

A number of facing preparations are currently in use to seal and disinfect a dentin surface following acid etching. These preparations typically include a monomeric resin capable of cross linking to the collagen fibers. Glutaraldehyde (GLUMA, Heraeus Kulzer, Inc.) and benzalkonium chloride (Healthdent, Inc.) are added as antimicrobials. These prior art antimicrobials are limited in their efficacy. Glutaraldehyde polymerizes in water and thereby the effective dosages decrease. Furthermore, glutaraldehyde is a known irritant as well as antiseptic and thereby may induce the dental hypersensitivity which the facing preparation is designed to prevent. Benzalkonium chloride is a potent antimicrobial yet is incompatible with anionic detergents such as soap, as well as with nitrates. While the benzalkonium cation is electrically attracted to dentin, stearic considerations prevent optimal interactions between the radical and dentinal tubules.

SUMMARY OF THE INVENTION

The present invention provides a facing preparation composition containing a polymerizable resin and an antimicrobial agent having the formula:

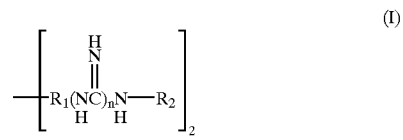

where $R_1$ is a hydrocarbon having between 1 and 16 carbon atoms, n is an integer between 1 and 8 inclusive, $R_2$ is selected from the group consisting of halophenyl and 2-ethylhexyl. Optionally, the antimicrobial agent is delivered in the form of an organic salt, with the anionic species selected from: acetate, gluconate, propionate, and acrylate. Optionally, a solvent is also provided to promote diffusion of the other composition components into a substrate. Solvents operative in the present invention illustratively include: methanol, water, acetone, methyl ethyl ketone, and isopropanol.

The present invention also provides for a facing preparation composition consisting essentially of: 28–55 weight percent polymerizable resin; 0.1–10 weight percent antimicrobial agent having the formula:

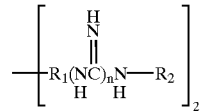

where $R_1$ is a hydrocarbon having between 1 and 16 carbon atoms, n is an integer between 1 and 6 inclusive, $R_2$ is selected from the group consisting of halophenyl and 2-ethylhexyl; 30–69.8% solvent and 0.1–10% benzalkonium chloride.

An antimicrobial oral rinse contains the antimicrobial agent present at greater than 0.2% by weight in a buccal cavity compatible solvent and excluding the polymerizable resin of the facing preparation composition.

DETAILED DESCRIPTION OF THE INVENTION

The present invention pertains to compositions for facing and disinfecting a calcified tissue structure. The facing preparation of the present invention inhibits thermal and microbial hypersensitivity in proximal nerves of the organism. The facing preparation of the present invention also promotes bonding of a subsequent structural sealing layer to the calcified tissue. The term "calcified tissue" as used herein is defined to mean periosteum, cortical bone, tooth enamel, cementum, dentin, and pulp. The present invention has particular utility in facing and disinfecting exposed dentin for subsequent bonding of additional restorative dental materials.

Optionally, calcified tissue substrates are etched by means conventional to the art, prior to application of a facing preparation of the instant invention. Acid etching generally involves application of mineral acids illustratively including phosphoric, nitric, citric and hydrofluoric acids. It is appreciated that mechanical etching using an abrasive grit is also operative herein. Following etching, extraneous acid and debris are removed from the substrate by irrigating the etched substrate with water. The substrate is then blotted or evaporatively dried by means illustratively including an air jet.

The facing preparation of the instant invention contains a polymerizable resin. The term "polymerizable resin" as defined herein means either a hydrophilic polymerizable compound having at least one hydroxyl moiety therein, a hydrophobic polymerizable hydrocarbon, or a polymerizable compound having both a hydrophobic and a hydrophilic moiety therein. Polymerizable resins operative within the present invention illustratively include hydroxyalkyl methacrylates, hydroxyalkyl acrylates, alkyl methacrylates, alkyl acrylates, polyhydric alcohols, mixtures thereof, substituted derivatives thereof and the like. Specific polymerizable resins operative within the present invention illustratively include 2-hydroxymethyl methacrylate (HMMA), 2-hydroxyethyl methacrylate (HEMA), bisphenol-A-glycidyl methacrylate prepolymer (bis-GMA), N-phenylglycine/glycidyl methacrylate (NPG-GMA), bis (glycerol dimethacrylate) phosphate, glycerol methacrylate, methyl acrylate, triethylene glycol dimethacrylate and the like. Preferably, hydrophilic resins such as HMMA and HEMA are used in facing preparations of the present invention which are tailored to treatment of inherently moist substrates, such as dentin. The facing preparations of the present invention preferably include a polymerizable resin present in amounts ranging from about 10–90% by weight relative to the total facing preparation weight. More preferably, the polymerizable resin is included in the facing preparation in amounts from 20–60 weight percent relative to the total facing preparation weight. Most preferably, the polymerizable resin is included in the facing preparation in amounts from 30–50 weight percent relative to the total facing preparation weight.

The facing preparation of the present invention optionally further includes a solvent. The solvent promoting diffusion of the facing preparation into microscopic pores and crevices of the substrate. The solvent is chosen to impart solubility on the polymerizable resin used in a particular facing preparation. In those instances where the osteoporotic substrate is dentin, hydrophilic solvents are preferred. Solvents operative within a facing preparation of the present invention illustratively include: ethanol, water, acetone, methyl ethyl ketone, and isopropanol. The solvent is preferably present in the facing preparation in amounts ranging from 10–90% relative to the total facing preparation weight. More preferably, the solvent is included in the facing preparation in an amount ranging from 20–80% by weight relative to the total facing preparation weight. Most preferably, the solvent is included in the facing preparation in an amount ranging from 30–70% by weight relative to the total facing preparation weight. It is appreciated that a miscible mixture of solvents is also operative herein.

The facing preparation of the present invention also includes an antimicrobial agent of the formula:

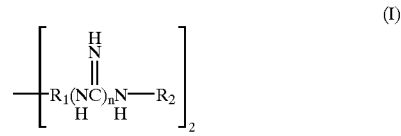

where $R_1$ is a hydrocarbon radical having between 1 and 16 carbon atoms, n is an integer between 1 and 8 inclusive and $R_2$ is selected from halophenyl and 2-ethylhexyl. It is appreciated that $R_1$ includes unsaturated hydrocarbon radicals, as well as heteroatom containing radicals. Preferably, the molecule of Formula (1) is associated with an adduct species. The adduct species being selected to promote solubility in the facing preparation. Adduct species operative in the present invention illustratively include: acetate, gluconate, propionate, and acrylate. Preferably, $R_1$ is a saturated hydrocarbon. Preferably, $R_1$ has between 1 and 6 carbon atoms. Preferably, the halophenyl is chlorophenyl. More preferably, the halophenyl is para-halophenyl. Specific antimicrobial agents of the present invention illustratively include: alexidine, chlorhexidine, alexidine gluconate, chlorhexidine gluconate, alexidine acetate, chlorhexidine acetate and chlorhexidine digluconate.

Both alexidine and chlorhexidine are effective antimicrobials against a wide range of vegative gram positive and gram negative organisms. The facing preparation of the present invention is preferably buffered to pHs ranging from about 5–9. More preferably, the present invention is buffered to pHs ranging from 6–9.

Optionally, a secondary biocide is introduced into the compositions of the present invention. Benzalkonium chloride is operative as an additive in the present invention compositions between 0.1 and 10% by weight of the total composition weights. It is appreciated that other additives, adjuvants, surfactants, stabilizers, dyes, and emulsifiers are also added optionally to the present invention. In particular, fluoride solution present to about 0.5% by weight is a well established wash effective against dental caries.

In another embodiment, solutions of the antimicrobial agent (I) are provided which lack the polymerizable resin. This solution has utility as an oral rinse to cleanse the buccal cavity and in particular tubules prior to application of conventional dental structures. While such rinses have previously been utilized having between about 0.12% to 0.20% chlorohexidine, considerably more effective antimicrobial formulations are disclosed herein. An antimicrobial rinse according to the present invention includes between 0.2 and 10% by weight of antimicrobial based on total solution weight. Preferably, the rinse contains 0.2 to 5% antimicrobial. More preferably, the rinse contains a solvent of water, acetone or ethanol or mixtures thereof.

It is appreciated that the facing preparation of the present invention may also include other conventional microbial agents which have a complementary antimicrobial spectrum to those of Formula I. The microbial agents of Formula I are particularly effective over time owing to charge interactions between the substrate and the agents of Formula I.

The following examples are given for the purpose of illustrating various embodiments of the invention and are not meant to limit the present invention in any way.

EXAMPLE 1

A dentin facing preparation is formed from the following components:

| Component | % by Weight of the Total Preparation |
| --- | --- |
| HEMA | 45 |
| Ethanol | 50 |
| Chlorhexidine | 5 |

Dentin is etched with a 40% phosphoric acid solution. The etched dentin is irrigated with water and dried with an air jet. The facing preparation is mixed and swabbed onto the dentin surface and allowed to air dry for about 20 seconds. The facing preparation is overlayered with a HEMA based polymerizable sealant Prodigy with Optibond Solo (Kerr Corp.). A strong filling persisted for greater than 6 months. The patient experienced no hypersensitivity associated with exposing the filled dentin cavity to hot water, bite pressure, or ice. The process is repeated and found to be repeatable with comparable sealant strengths.

EXAMPLE 2

A dentin facing preparation is formed of the following components:

| Component | % by Weight of the Total Preparation |
| --- | --- |
| HMMA | 40 |
| Water | 59 |
| Chlorhexidine gluconate | 1 |

This facing preparation composition behaves similarly to the composition of the primer in Example 1.

EXAMPLE 3

A dentin facing preparation is formed from the following components:

| Component | % by Weight of the Total Preparation |
| --- | --- |
| HEMA | 50 |
| Ethanol | 30 |
| Water | 10 |
| Chlorhexidine acetate hydrate | 10 |

This facing preparation composition behaves similarly to the composition of the facing preparation in Example 1.

EXAMPLE 4

A dentin facing preparation is formed from the following components:

| Component | % by Weight of the Total Preparation |
| --- | --- |
| HEMA | 40 |
| Water | 50 |
| Alexidine gluconate | 5 |
| Benzalkonium chloride | 5 |

This facing preparation composition behaves similarly to the composition of the facing preparation in Example 1.

EXAMPLE 5

A cementum facing preparation is formed from the following components:

| Component | % by Weight of the Total Preparation |
| --- | --- |
| Glycerol methacrylate | 28 |
| Ethanol | 18 |
| Water | 48 |
| Chlorhexidine gluconate | 6 |

The facing preparation prevented cervical infection and afforded good bond strength when a subsequent bis-GMA sealant resin is applied.

EXAMPLE 6

A cortical bone facing preparation is formed from the following components:

| Component | % by Weight of the Total Preparation |
| --- | --- |
| HMMA | 55 |
| Water | 41 |
| Chlorhexidine | 3 |
| Ciprofloxin | 1 |

The facing preparation promoted adhesion to a cyanomethacrylate based bonding material.

EXAMPLE 7

The in vitro tensile bond strength of a conventional tooth bonding composite Prodigy with Optibond Solo (Kerr Corp.) is measured with and without the dentin facing preparation of Example 1. Bond strength and failure modes are determined for bonding to superficial and deep dentin sites.

| | Superficial Dentin | Deep Dentin |
| --- | --- | --- |
| | Bond Strength, MPa | |
| Control | 27 ± 13 | 28 ± 8 |
| With facing preparation of Example 1 | 36 ± 11 | 29 ± 6 |

| | Superficial Dentin | Deep Dentin |
|---|---|---|
| | Failure Sites, % | |
| Control | 54A/46C | 44A/26C/30T |
| With facing preparation of Example 1 | 22A/68C/10T | 46A/48C/6T | where A is an adhesive failure at the tooth-composite surface, C is cohesive failure in the composite and T is a cohesive failure in the dentin.

EXAMPLE 8

Standardized cultures of Strept. mutans are grown in petri dishes and subjected to 30 second submersion in 20 milliliters of various concentration rinses of aqueous chlorohexidine. A 0.04% chlorohexidine solution and water serve as controls. Thereafter, the petri dishes are incubated and colony members counted after 48 hours.

| Chlorohexidine Concentration (wt. %) | Colony Member After Rinse |
|---|---|
| 0 | 196 |
| 0.04 | 26 |
| 0.2 | 0 |
| 0.5 | 1 |
| 1.0 | 1 |
| 2.0 | 0 |
| 5.0 | 2 |
| 10.0 | 0 |

Those skilled in the art will readily appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon considering the specification and following claims.

What is claimed is:

1. A facing preparation composition comprising:
   a polymerizable acrylate resin suitable for bonding a filling; and
   a 0.1–10 weight percent antimicrobial agent having the formula:

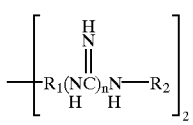
(I)

where $R_1$ is a hydrocarbon having between 1 and 16 carbon atoms, n is an integer between 1 and 8 inclusive, $R_2$ is selected from the group consisting of halophenyl and 2-ethylhexyl, and wherein said antimicrobial agent is coupled to a solubility promoting adduct species.

2. The facing preparation composition of claim 1 wherein said composition is 28–55% by weight of said resin; and 0.1–10% by weight of said antimicrobial.

3. The facing preparation composition of claim 2 wherein said antimicrobial is chlorhexidine.

4. The facing preparation composition of claim 2 wherein said antimicrobial is alexidine.

5. A facing preparation composition comprising:
   28–55 weight percent polymerizable resin suitable for bonding a filling;
   0.1–10 weight percent antimicrobial agent having the formula:

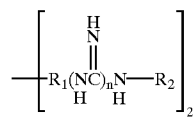

where $R_1$ is a hydrocarbon having between 1 and 16 carbon atoms, n is an integer between 1 and 6 inclusive, $R_2$ is selected from the group consisting of halophenyl and 2-ethylhexyl and wherein said antimicrobial agent is coupled to a solubility promoting adduct species;
   30–69.8% solvent; and
   0.1–10% benzalkonium chloride.

6. The facing preparation of claim 1 wherein said solubility promoting adduct species is selected from the group consisting of: acetate, gluconate, propionate, and acrylate.

7. The facing preparation of claim 1 where $R_1$ is N-propyl and n is 2.

8. The facing preparation of claim 6 wherein said antimicrobial agent is chlorhexidine gluconate.

9. The facing preparation of claim 6 wherein said antimicrobial agent is chlorhexidine diacetate hydrate.

10. The facing preparation composition of claim 1 further comprising a solvent compatible with biological tissue.

11. The dental facing preparation of claim 10 wherein said solvent is selected from the group consisting of water, ethanol, acetone and ethyl methyl ketone.

12. The facing preparation composition of claim 11 wherein said composition is 28–55% by weight of said resin; and 0.1–10% by weight of said antimicrobial; and 35–71.9% of said solvent.

13. A process for cleansing a dentin tubule prior to application of a dental structure, the process comprising the steps of:
   (a) swabbing a tooth surface with an antimicrobial mixture, the mixture comprising at least 0.2% by weight of an antimicrobial agent having the formula:

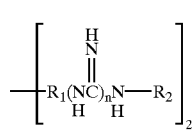
(I)

where $R_1$ is a hydrocarbon having between 1 and 16 carbon atoms, n is an integer between 1 and 8 inclusive, $R_2$ is selected from the group consisting of halophenyl and 2-ethylhexyl, and a buccal cavity compatible solvent; and
   (b) applying the dental structure.

14. The rinse of claim 13 wherein said antimicrobial agent is present from 0.2 to 10% by weight.

15. The rinse of claim 14 wherein said antimicrobial agent is present from 0.2 to 5% by weight.

16. The process of claim 13 wherein said antimicrobial of Formula I is coupled to an adduct species, said species selected from the group consisting of: acetate, gluconate, propionate, and acrylate.

17. The process of claim 16 wherein said antimicrobial agent is chlorhexidine gluconate.

18. The process of claim 16 wherein said antimicrobial agent is chlorhexidine diacetate hydrate.

19. The process of claim 13 wherein said solvent is selected from the group consisting of water, ethanol, acetone and ethyl methyl ketone.

20. A method for preparing a tooth for a dental procedure comprising the steps of:
   (a) priming a tooth for application of a dental facing composition;
   (b) providing the dental facing composition wherein the composition comprises a polymerizable acrylate resin, 0.1–10 weight percent of an antimicrobial agent having the formula:

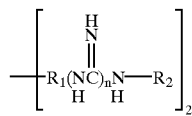

(I)

where $R_1$ is a hydrocarbon having between 1 and 16 carbon atoms, n is an integer between 1 and 8 inclusive, $R_2$ is selected from the group consisting of halophenyl and 2-ethylhexyl and wherein the antimicrobial agent is coupled to a solubility promoting adduct species; and (c) applying the dental facing composition to the tooth surface, wherein the application of the dental facing composition prepares the tooth for the dental procedure.

21. A commercial package comprising a polymerizable resin and a compound of Formula I according to claim 1 together with instructions for the use thereof as a dental facing preparation.

22. The method of claim 20 wherein the priming is by a method selected from the group consisting of: cleaning and etching.

23. The method of claim 20 where $R_1$ is N-propyl and n is 2.

24. The method of claim 20 where said antimicrobial agent is chlorhexidine gluconate.

25. The method of claim 20 where said antimicrobial agent is chlorhexidine diacetate hydrate.

26. The method of claim 20 further comprising a solvent compatible with biological tissue.

27. The method of claim 20 wherein said solvent is selected from the group consisting of water, ethanol, acetone and ethyl methyl ketone.

* * * * *

UNITED STATES PATENT AND TRADEMARK OFFICE
CERTIFICATE OF CORRECTION

PATENT NO. : 6,494,717 B1
DATED : December 17, 2002
INVENTOR(S) : Pelerin

It is certified that error appears in the above-identified patent and that said Letters Patent is hereby corrected as shown below:

Column 1,
Line 57, replace "is." with -- is --.

Column 2,
Line 45, Replace "$\left[ \begin{array}{c} H \\ | \\ R_1 (NC)_n \; N\square \text{---} R_2 \\ | \quad | \\ H \quad H \end{array} \right]_2$" with -- $\left[ \begin{array}{c} H \\ | \\ R_1 (NC)_n \; N\square\text{---} R_2 \\ | \quad | \\ H \quad H \end{array} \right]_2$ 5 --.

Signed and Sealed this

Eighth Day of July, 2003

JAMES E. ROGAN
*Director of the United States Patent and Trademark Office*